United States Patent [19]

Besemer et al.

[11] Patent Number: 5,585,114
[45] Date of Patent: Dec. 17, 1996

[54] COMPOSITION FOR CONTROLLED RELEASE OF AN ACTIVE SUBSTANCE AND METHOD FOR THE PREPARATION OF SUCH A COMPOSITION

[75] Inventors: Arie C. Besemer, Amerongen; Coenraad F. Lerk, Peize, both of Netherlands

[73] Assignee: Nederlandse Organisatie Voor Toegepast-Natuurwetenschappelijk Onderzoek Tno, Delft, Netherlands

[21] Appl. No.: 356,256

[22] PCT Filed: Jul. 2, 1993

[86] PCT No.: PCT/NL93/00140

§ 371 Date: Feb. 28, 1995

§ 102(e) Date: Feb. 28, 1995

[87] PCT Pub. No.: WO94/01092

PCT Pub. Date: Jan. 20, 1994

[30] Foreign Application Priority Data

Jul. 3, 1992 [NL] Netherlands .............................. 9201195

[51] Int. Cl.$^6$ ...................................................... A61K 9/14
[52] U.S. Cl. ............................................ 424/488; 424/484
[58] Field of Search ...................................... 424/484, 485, 424/486, 487, 488

[56] References Cited

U.S. PATENT DOCUMENTS

| | | |
|---|---|---|
| 3,490,742 | 1/1970 | Nichols et al. . |
| 3,493,652 | 2/1970 | Hartman . |
| 5,047,248 | 9/1991 | Calanchi et al. .......................... 424/485 |
| 5,456,921 | 10/1995 | Mateescu et al. ....................... 424/465 |

FOREIGN PATENT DOCUMENTS

| | | |
|---|---|---|
| 0343993 | 11/1989 | European Pat. Off. . |
| 63-104925 | 5/1988 | Japan . |
| 1072795 | 6/1967 | United Kingdom . |
| WO85/03414 | 8/1985 | WIPO . |
| WO87/05212 | 9/1987 | WIPO . |
| WO89/00045 | 1/1989 | WIPO . |

Primary Examiner—John C. Bleutge
Assistant Examiner—Robert H. Harrison
Attorney, Agent, or Firm—Young & Thompson

[57] ABSTRACT

Composition for delayed release of an active substance, such as a medicament, the active substance being incorporated in a polysaccharide matrix which is formed by an essentially crystalline straight-chain glucan, in particular an α-glucan which has a helix structure, such as amylodextrin or a fraction having a helix structure obtained from amylose V. The composition can contain an amount of active substance of from 0.1 to 80% by weight and the active substance can, depending of the hydrophilicity, have a molecular weight of up to 500 to 1500 daltons. The active substance is released from the composition at a constant rate.

10 Claims, 8 Drawing Sheets

COMPOSITION FOR CONTROLLED RELEASE OF AN ACTIVE SUBSTANCE AND METHOD FOR THE PREPARATION OF SUCH A COMPOSITION

The invention relates to a composition for delayed release of an active substance in a target environment, the active substance being incorporated in a polysaccharide matrix.

Compositions for delayed release of an active substance, for example for delayed release of a medicament for oral administration in the gastrointestinal tract of a mammal, have advantages, inter alia because the administration of the active substance can take place in a small number of doses and because a more constant concentration is obtained in the target environment.

Compositions for delayed release are known in diverse forms. One form of delayed release can comprise the presence of a matrix containing the active substance therein, which matrix slowly dissolves in the water-containing environment and thus releases the active substance in a delayed manner; a composition of this type is, for example, disclosed in European Patent Application EP-A-241,179. A composition of this type in which the matrix is formed by a natural polysaccharide such as xanthan is disclosed in International Patent Application WO-A-87,05212. According to a variant thereof, the active substance is packaged in an insoluble capsule which is provided with a water-soluble stopper, as disclosed, inter alia, in British Patent Application 2,241,485.

Another form of a composition for delayed release is a composition from which the active substance is released by erosion, as is disclosed, for example, in European Patent Application EP-A-381,182.

Compositions for delayed release in which the matrix material is a β-glucan, such as cellulose or a cellulose derivative, are disclosed, inter alia, in International Patent Application WO-A-88,10284 and Netherlands Patent Application 87,02294 (=GB-A-2,195,893). The use of heat-modified starch as the matrix for the controlled release of medicaments for oral administration is described by J. Herman and J. P. Remon, *Int. J. Pharmaceutics*, 56, 51–63 and 65–70 (1989).

Amylose, a straight-chain starch fraction, has also been proposed as a carrier material for active compounds: British Patent 1,072,795 describes the use of "retrograded" amylose, i.e. associated amylose; EP-A-343,993 discribes the use of "glassy" amylose, i.e. one of the types of amorphous amylose, as a release-delaying material for active substances.

The known compositions for the delayed release of an active substance frequently have the disadvantage that release of the active substance does not proceed in accordance with an ideal zero order rate, that is to say with a constant amount per unit time, but at a first order rate, that is to say with an amount which decreases per unit time, or poorer; in addition, the materials used as matrix are often expensive.

The aim of the invention is to provide a composition, and a method for the preparation thereof, which releases an active substance as far as possible in accordance with a zero order curve and which, in addition, is harmless to health and/or the environment and which, moreover, is economical in use.

This aim is achieved by means of a composition according to the invention which to this end is characterised in that the matrix material in which the active substance is incorporated comprises an essentially crystalline, straight-chain glucan. The glucan is preferably an α-glucan and in particular an α-1,4-glucan and preferably has essentially a helix structure.

An α-1,4-glucan is understood to be an essentially straight-chain polysaccharide which is composed of anhydroglucose units which are linked to one another by α-bridges via the 1-position and 4-position. Other straight-chain glucans (polysaccharides) can also be used if these are able to assume a helical structure, such as, for example, β-1,3-glucans.

Suitable α-1,4-glucans are in general starch fractions and starch derivatives. The α-1,4-glucan can, for example, be an amylose. Amylose is a straight chain of α-1,4-anhydroglucose units which has a degree of polymerisation (DP) of the order of 100–1,000. One form of amylose is so-called amylose V (Avebe). an amylose which has an amorphous structure and is precipitated from an aqueous solution by magnesium sulphate. Use is made of a product having a crystalline structure which may be derived from amylose V. This so-called helical amylose or crystalline amylose can be obtained from amylose by dissolving in water and complexing with a complex-forming agent such as 1-butanol, after which the complex-forming agent can be removed by careful spray-drying or by treatment with a suitable solvent, such as ethanol, methanol or acetone. The fractionation of amylose using complex-forming agents is disclosed by W. Dvonch et al., *J. Am. Chem. Sec.*, 72, 1748–1750 (1950) and S. Lansky et al. *ibid.*, 71, 4066–4075 (1949).

The crystalline and/or helical amylose to be used in the compositions according to the invention can also be obtained directly from starch, in a similar process using a complexing agent, further including washing the complex to remove amylopectin.

Suitable complexing agents for preparing crystalline, helical amylose by precipitating amylose from an aqueous solution are known in the art. They include 1,1,2,2-tetrachloroethane, cyclohexane, 1,1,1- and 1,1,2-trichloroethane, benzene, chloroform, fluorobenzene, o-xylene, 2,3-dimethylbutane. $C_3$–$C_8$ alcohols and phenols, such as butanol, amyl alcohol, cyclohexanol, hexanol and 2-octanol, isopropyl ketone, quinoline, chloral hydrate, butyric acid etc. See e.g. J. Muetgeert, *Advances in Carbohydrate Chemistry*, Vol. 16 Ed. Melville, Wolfrom, Acad. Press (1961).

Derivatives which are obtained by debranching branched glucans, in particular amylopectins, are also suitable. To this end the α-1,6 bonds of amylopectin are broken, preferably enzymatically (see Kobayashi, S. et al., *Cereal Chem.* 63. 71–74 (1968) and Netherlands patents 160,615 and 165,500) with the formation of amylodextrin, a straight-chain dextrin. This has an average chain length (DP) of the order of 15–75, with a maximum between 15 and 25 and a maximum between 45 and 75. Amylodextrin, like the helical amylose, occurs in helix form with approximately 6 to 7 anhydroglucose units per winding.

The crystalline α-1,4-glucans suitable for use in the present compositions can be distinguished from unsuitable types of glucans by their infrared spctrum. The crystalline amylose and amylodextrin, just like cyclodextrin, have sharp absorptions at about 1150, 1080 and 1020 $cm^{-1}$, whereas amorphous amylose only exhibits broad or undistinguished absorptions at these frequencies.

Surprisingly, it has been found that tablets and other administration forms which comprise such crystalline straight-chain glucans as matrix-forming material are subject to little or no disintegration and little or no attack by α-amylase, an enzyme which usually splits starch, for example in the digestive tract, or by acid. In addition, the tablets are found to be resistant to breaking and often more resistant to breaking than microcrystalline cellulose (for example Avicel®).

Preferably, the matrix material contains at least 5% by weight of water. If the material contains less than 5% of water a usable release pattern is obtained but the strength is then no better than that, or even worse than that, of microcrystalline cellulose. Preferably, the material contains no more than 25% by weight, and more preferably no more than 20% by weight of water. In particular, the matrix material contains 7–16% by weight of water.

In addition, the matrix material can contain other fillers and auxiliaries. Thus, the presence of non-crystalline amylose up to a content of, for example, 25% by weight does not interfere. Many types of starch contain about 25% of amylose and if these starches is used to prepare amylodextrin by debraching the amylopectin, this residual amylose therefore does not have to be removed if the starch is used as starting material for the matrix-forming material.

Suitable auxiliaries are the auxiliaries known per se for compositions of active substances, such as lubricants, for example magnesium stearate, auxiliary solvents, pH regulators, preservatives, disintegrating agents, colorants, flavourings and the like.

Auxiliaries which modify the release pattern of the active substance from the matrix, such as auxiliaries which in themselves are inactive, for example lactose, or active auxiliaries such as α-amylase, which can help the matrix material to disintegrate from inside to out, can also advantageously be present.

The active substance can be present in the matrix material in virtually any desired concentration. In general, the amount of active substance can make up, for example, 0.1–80% by weight of the composition, partly depending on the desired dosage. More particularly, the amount is between 0.5 and 50% by weight. Within this range, a release rate is obtained which is independent of the remaining amount of active substance, that is to say which has a zero order curve. This is also an unexpected aspect of the compositions according to the invention.

The rate of release of the composition according to the invention can be adjusted by varying one or more of the following parameters: active substance concentration in the matrix material, dosage unit form, in particular the surface area/capacity ratio, force under which the composition is pressed, presence of disintegration-promoting agents, for example lactose or α-amylase, or disintegration-retarding agents, such as a coating or an inert filler.

The active substance can be of diverse natures. For example it can be medicaments for oral, rectal, vaginal or transdermal administration, diagnostic agents, feedstuffs or conditioning agents, flavourings, manure or nutrients to be added to water or soil, preservatives, vaccine substances, hormones, genetic material, control agents, attractants, growth promoters and the like. The active substances can be either organic or inorganic. Mixtures of active substance can also be administered by means of the composition according to the invention. Release can take place in an aqueous medium, such as the gastrointestinal tract of animals, or in plants or in the soil, but also into the air.

The composition according to the invention is suitable, in particular, for the controlled release of substances of low molecular weight, such as those having a molecular weight of less than 1,000 daltons (D). If the active substance is released into an aqueous medium, the hydrophilicity of the active compound is also of importance for the rate of release. Thus, hydrophilic substances having a molecular weight of up to about 1,500 Da still be effectively released, whilst for hydrophobic substances the practical upper limit will be at about 500 Da.

The composition can also be provided with a coating which provides further protection or further control or the release or, for example, has a colouring or taste function. The composition can also be in the form of a capsule in which the matrix material containing active substance is present, for example in granular form or powder form.

The composition according to the invention can be in any desired form, such as tablets, powders, granules, plasters and implants.

Tablets can be pressed directly after mixing the active substance with the straight-chain glucan as matrix material and any other auxiliaries. Preferably, however, the mixture is granulated before or after physical mixing of the active substance and matrix material and is then tableted.

EXAMPLE I

Figure 1:
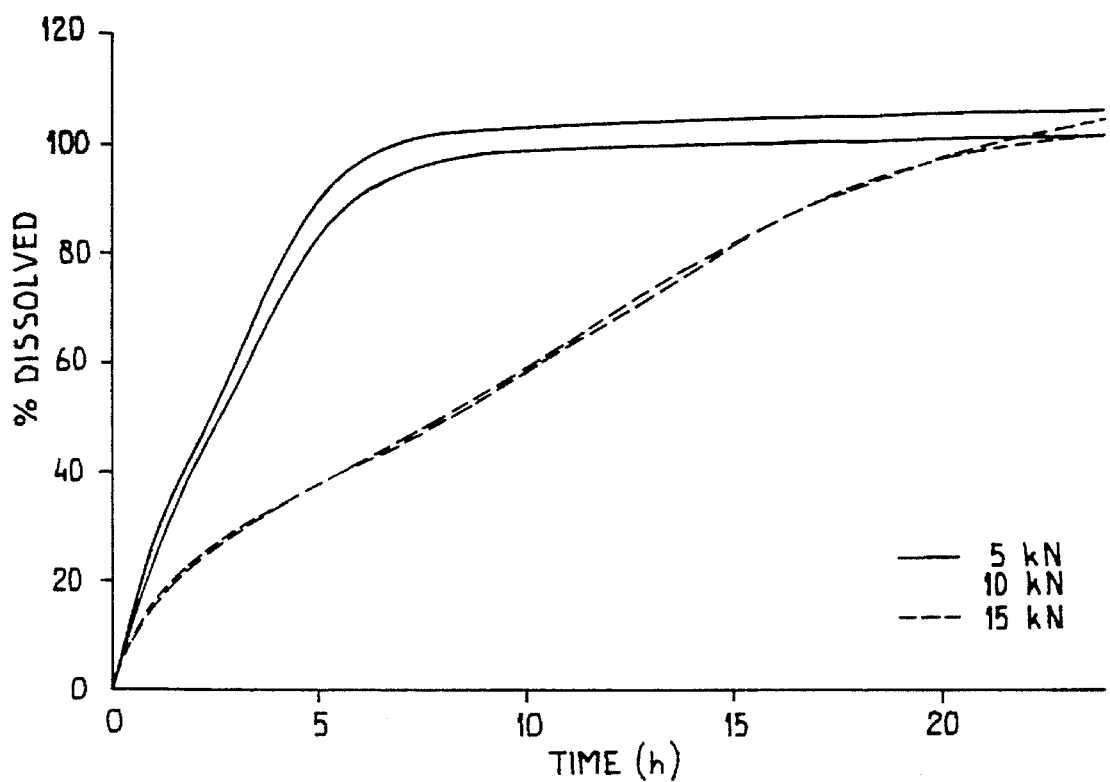
FIGS. 1 and 2 are graphs of the percentage of the original amount of Theophylline that has gone into solution, with time, for respectively 75% and 10% of active substance.

The release of theophylline from amylodextrin matrix tablets containing 75% of active substance was determined. After mixing and dry granulating a mixture of amylodextrin and theophylline, the granules were compressed under a force of, respectively, 5 kN, 10 kN and 15 kN. The tablets weighed 300 mg, comprising 225 mg of theophylline (=75%) and about 9% of water, and had a diameter of 9 mm. Release of the active substance from the tablet was determined in an aqueous medium, buffer pH 6.8, over a period of 24 hours and is shown in FIG. 1 as a percentage of the original amount which has gone into solution.

EXAMPLE II

Figure 2:
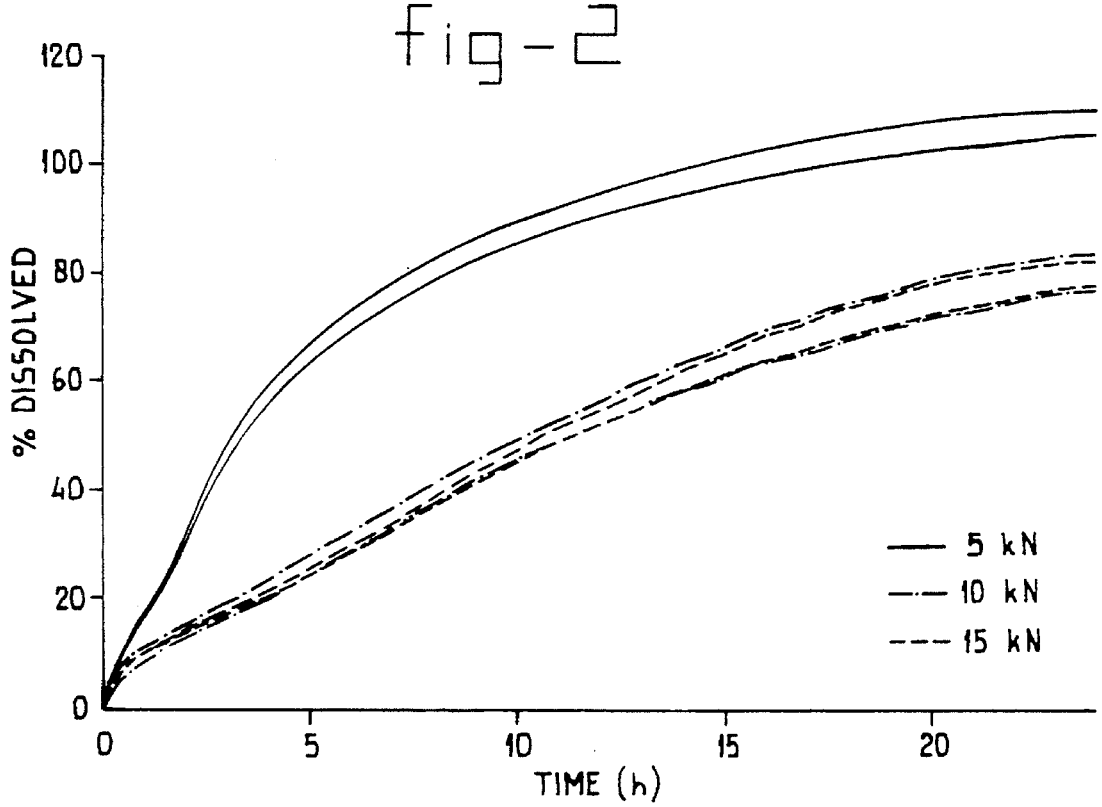

The release of theophylline from amylodextrin matrix tablets containing 10% of active substance was determined. After mixing and dry granulating a mixture of amylodextrin and theophylline, the granules were compressed under a force or, respectively, 5 kN, 10 kN and 15 kN. The tablets weighed 300 mg, comprising 30 mg of theophylline (=10%) and 32 mg of water (10.7%), and had a diameter of 9 mm. Release of the active substance from the tablet was determined in an aqueous medium, buffer pH 6.8, over a period of 24 hours and is shown in FIG. 2 as a percentage of the original amount which has gone into solution.

EXAMPLE III

Figure 3:
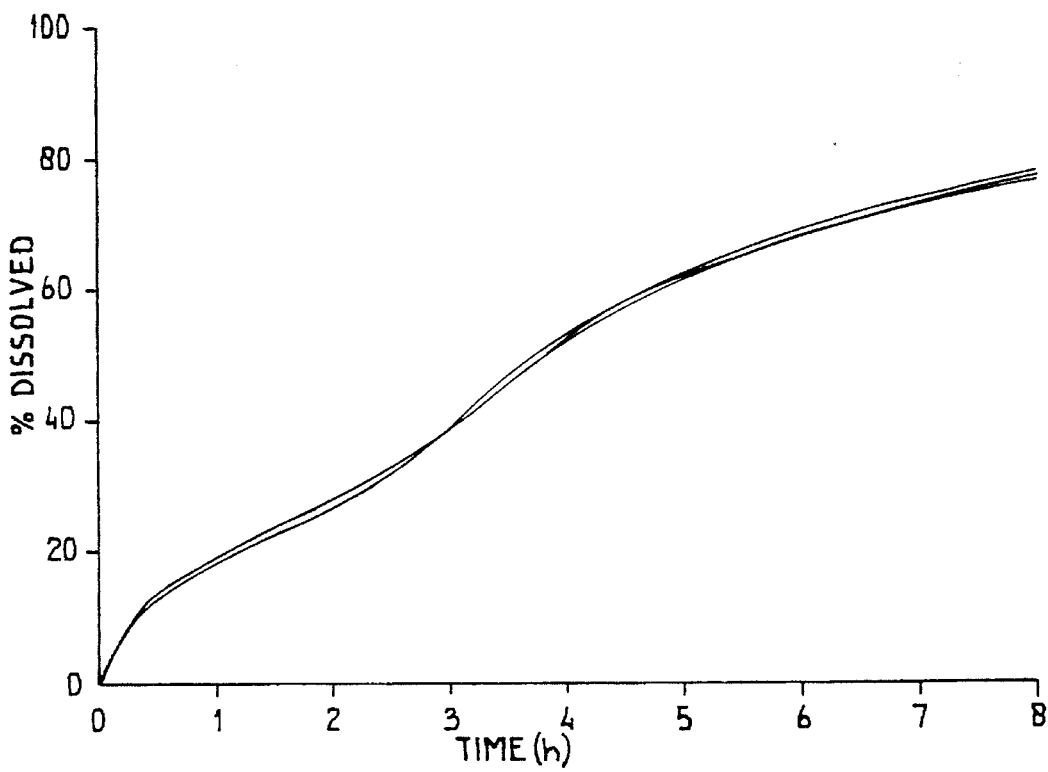
FIG. 3 is similar to FIGS. 1 and 2, but pertains to paracetamol.

The release of paracetamol from amylodextrin matrix tablets containing 30% of active substance was determined. After mixing amylodextrin and paracetamol, tablets were struck under a force of 10 kN. The tablets weighed 300 mg, comprising 90 mg of paracetamol (=30%) and about 9% of water, and had a diameter of 9 mm. The release of the active substance was determined from 3 tablets in an aqueous medium, buffer pH 6.8, over a period of 8 hours and is shown in FIG. 3 as a percentage of the original amount which has gone into solution.

EXAMPLE IV

Figure 4:
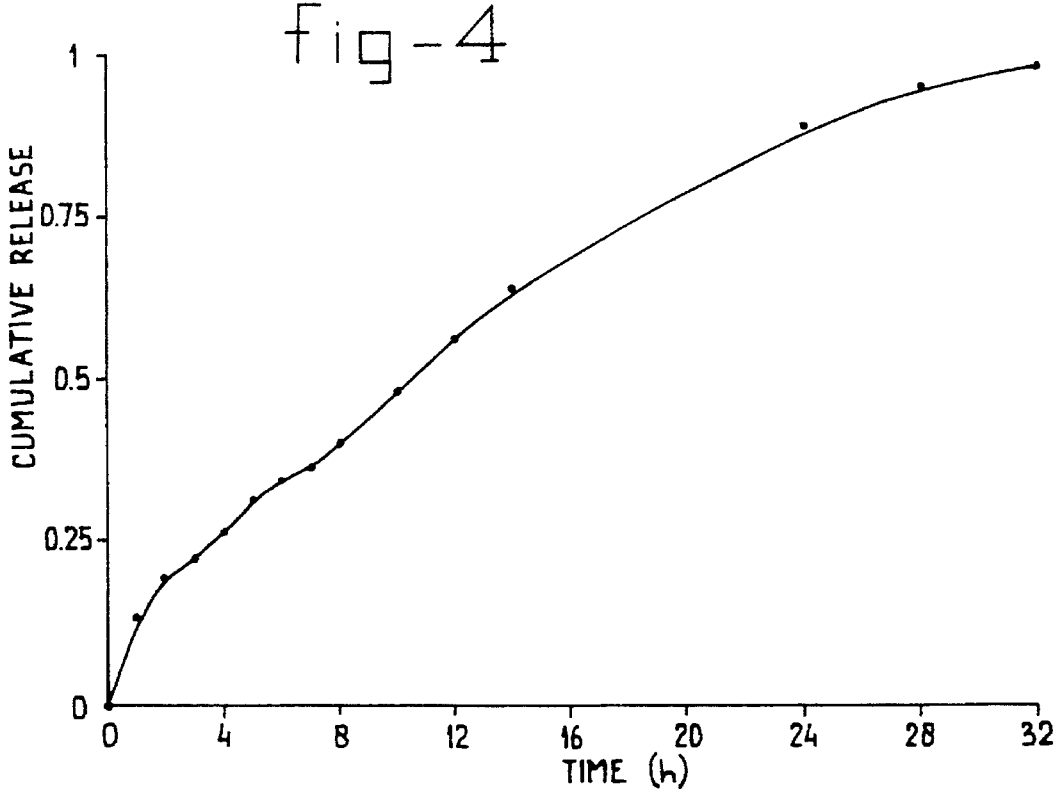
FIG. 4 is similar to FIG. 3 but shows the in vivo absorption of paracetamol.
Figure 5:
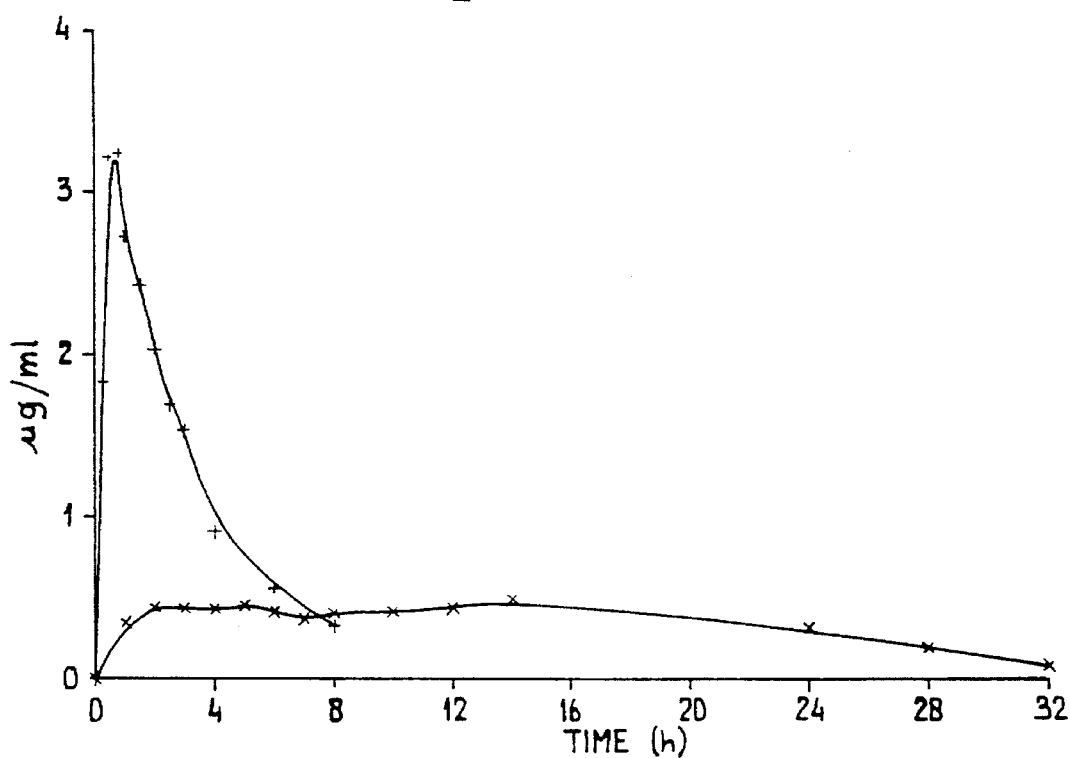
FIG. 5 shows the in vivo blood levels after administration of tablets according to the invention (+) and in vivo blood levels after direct administration (*) for paracetamol.

The in vivo absorption of paracetamol from amylodextrin matrix tablets containing 30% of active substance was determined. After mixing amylodextrin and paracetamol, tablets were struck under a force of 10 kN. The tablets weighed 333 mg, comprising 100 mg of paracetamol (=30%), and had a diameter of 9 mm. Three tablets, corresponding to a dosage of 300 mg of paracetemol, were taken by a test person. The cumulative absorption over a period of 32 hours was calculated on the basis of the blood levels determined. This cumulative absorption is shown in FIG. 4. The blood levels which resulted from administration of the composition according to the invention (+) and those resulting from direct administration (*) are shown in FIG. 5.

EXAMPLE V

Figure 6:
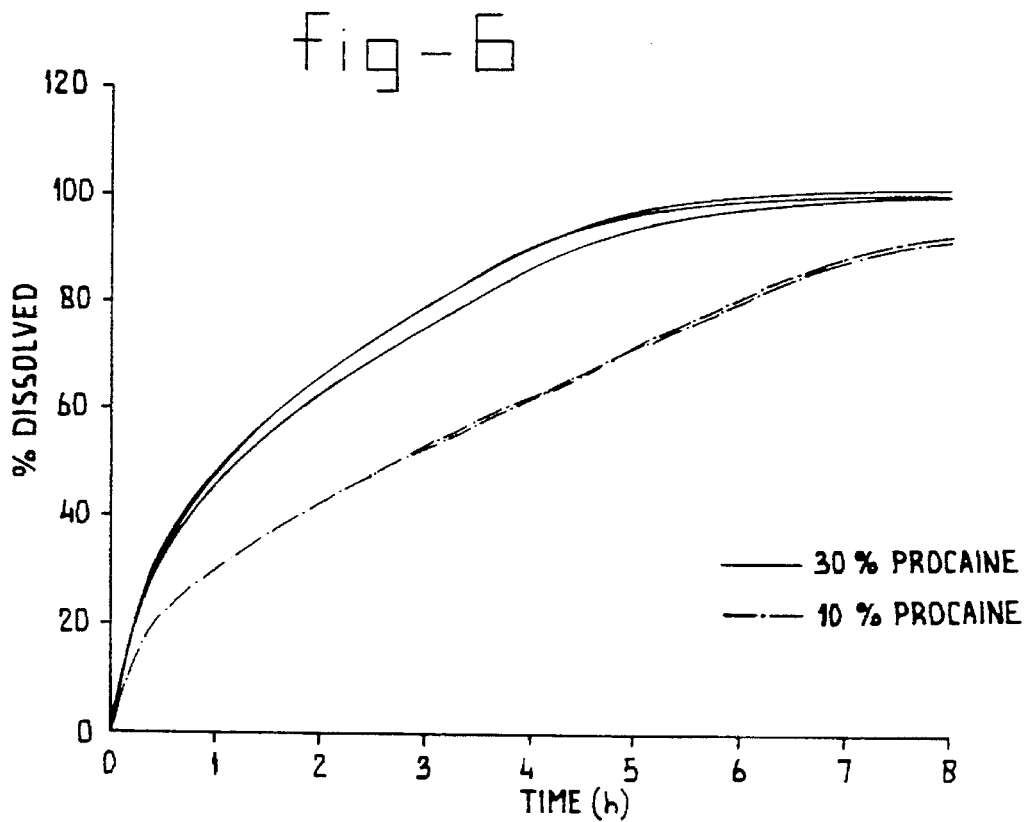
FIG. 6 is a graph of the release of procaine hydrochloride.

The release of procaine.HCl from amylodextrin matrix tablets containing 10 and 30% respectively of active substance was determined. After mixing amylodextrin and procaine.HCl, tablets were struck under a force of 10 kN. The tablets weighed 300 mg, comprising, respectively, 30 and 90 mg of procaine.HCl (=10 and 30%), and had a diameter of 9 mm. Release of the active substance from the tablet was determined in an aqueous medium, buffer pH 6.8, over a period of 8 hours and is shown in FIG. 6.

EXAMPLE VI

Figure 7:
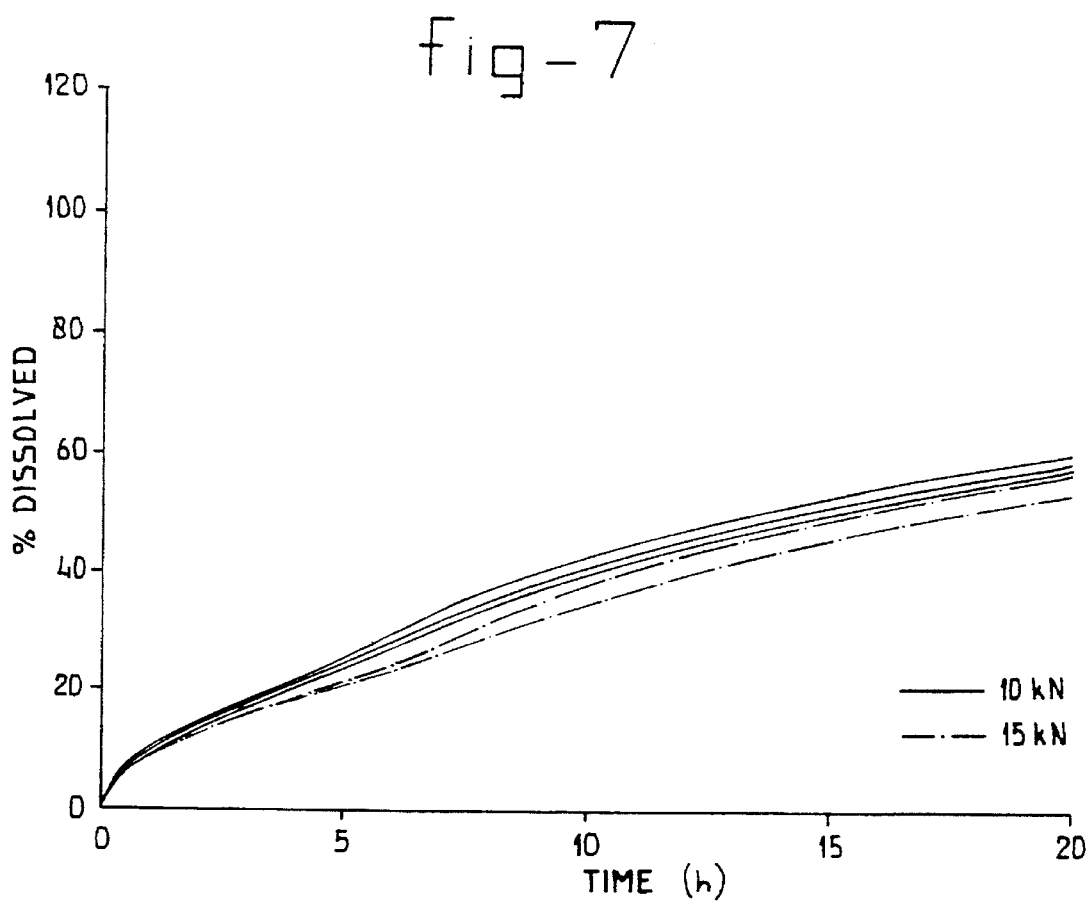
FIG. 7 is a graph showing the release of methylparaben.

The release of methylparaben from amylodextrin matrix tablets containing 30% of active substance was determined. After mixing amylodextrin and methylparaben, tablets were struck under a force of, respectively, 10 kN and 15 kN. The tablets weighed 300 mg, =comprising 90 mg of methylparaben (=30%), and had a diameter of 9 mm. Release of the active substance from the tablet was determined in an aqueous medium, buffer pH 6.8, over a period of 20 hours and is shown in FIG. 7.

EXAMPLE VII

Figure 8:
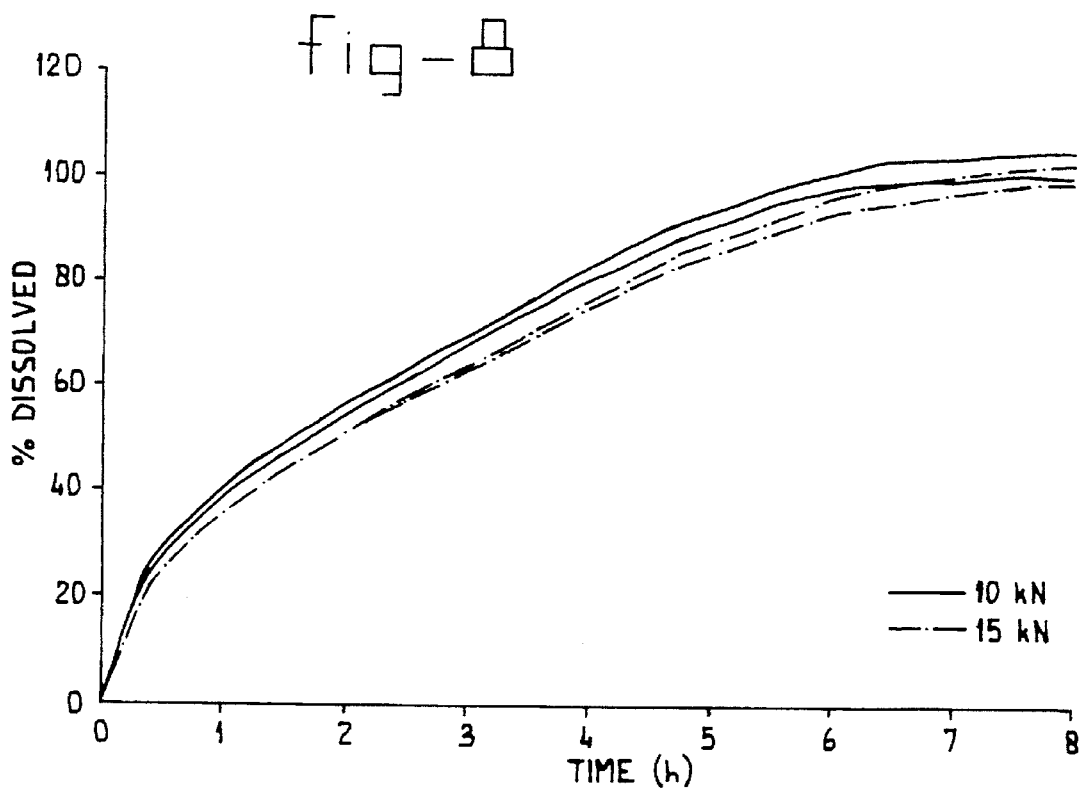
FIG. 8 is a graph of the dissolution of tablets containing 30% potassium dichromate.

Amylodextrin matrix tablets containing 30% of potassium dichromate were prepared. After mixing amylodextrin and potassium dichromate and 0.5 % of magnesium stearate (a tableting auxiliary which is used as lubricant), tablets were struck under a force of, respectively, 10 kN and 15 kN. The tablets weighed 300 mg, comprising 90 mg of potassium dichromate (=30%) and had a diameter of 9 mm. Release of the active substance from the tablet was determined in an aqueous medium, buffer pH 6.8, over a period of 20 hours and is shown in FIG. 8.

EXAMPLE VIII

Figure 9:
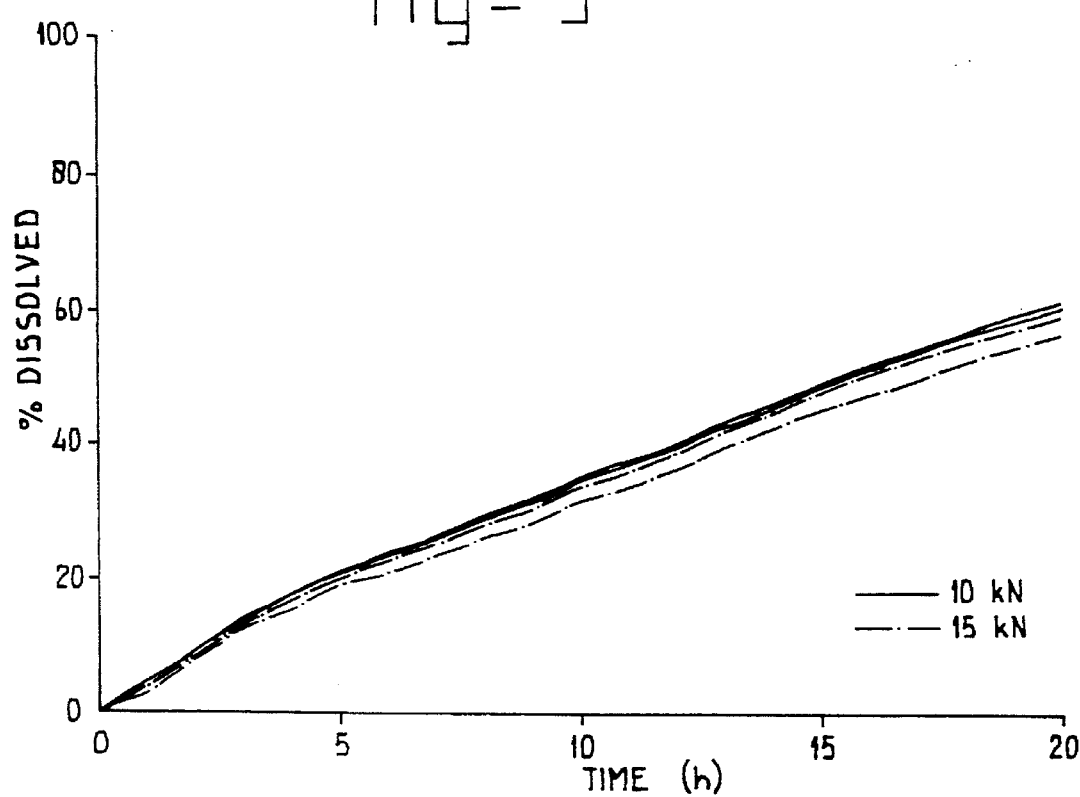
FIG. 9 is a graph of the release of diazepam.

The release of diazepam from amylodextrin matrix tablets containing 5% by weight of active substance was determined. After mixing amylodextrin and diazepam, tablets were struck under a force of, respectively, 10 kN and 15 kN. The tablets weighed 300 mg, comprising 15 mg of diazepam (=5%) and had a diameter of 9 mm. Release of the active substance from the tablet was determined in an aqueous medium, buffer pH 6.8, over a period of 20 hours and is shown in FIG. 9.

EXAMPLE IX

Figure 10:
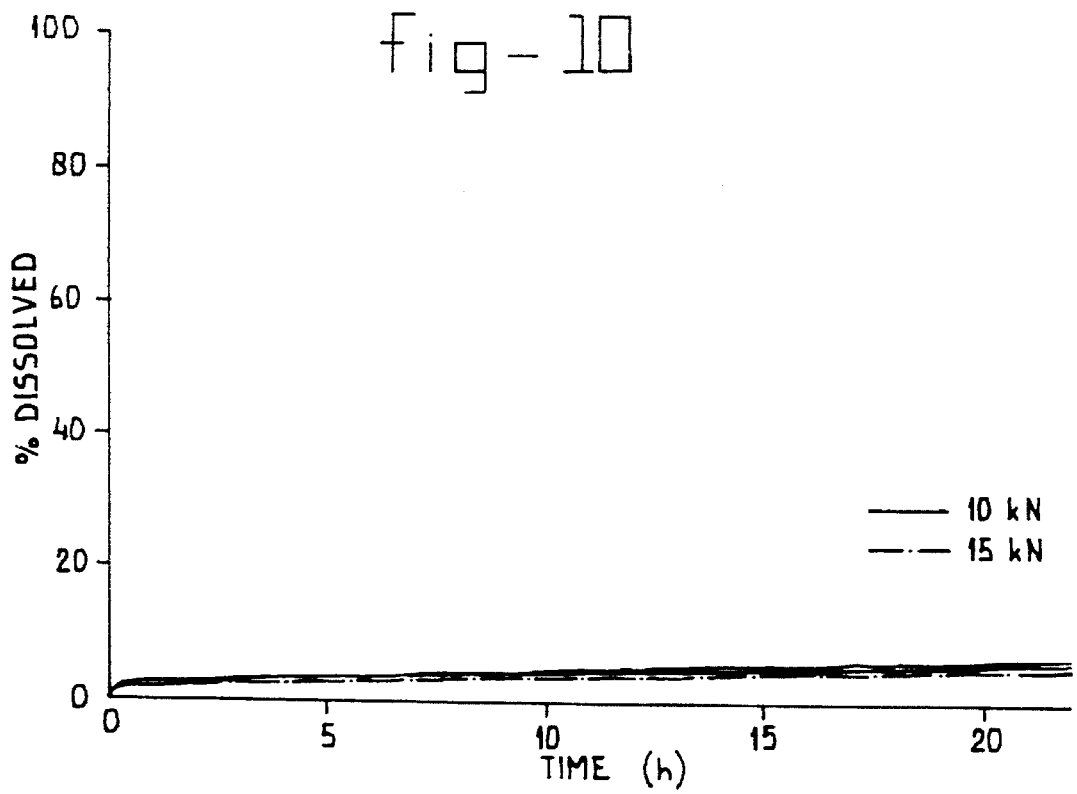
FIG. 10 is a graph of the release of prednisolone.

The release of prednisolone from amylodextrin matrix tablets containing 30% by weight of active substance was determined. After mixing amylodextrin and prednisolone, tablets were struck under a force of, respectively, 10 kN and 15 kN. The tablets weighed 300 mg, comprising 90 mg of prednisolone (=30%), and had a diameter of 9 mm. Release of the active substance from the tablet was determined in an aqueous medium, buffer pH 6.8, over a period of 20 hours and is shown in FIG. 10.

EXAMPLE X

Figure 11:
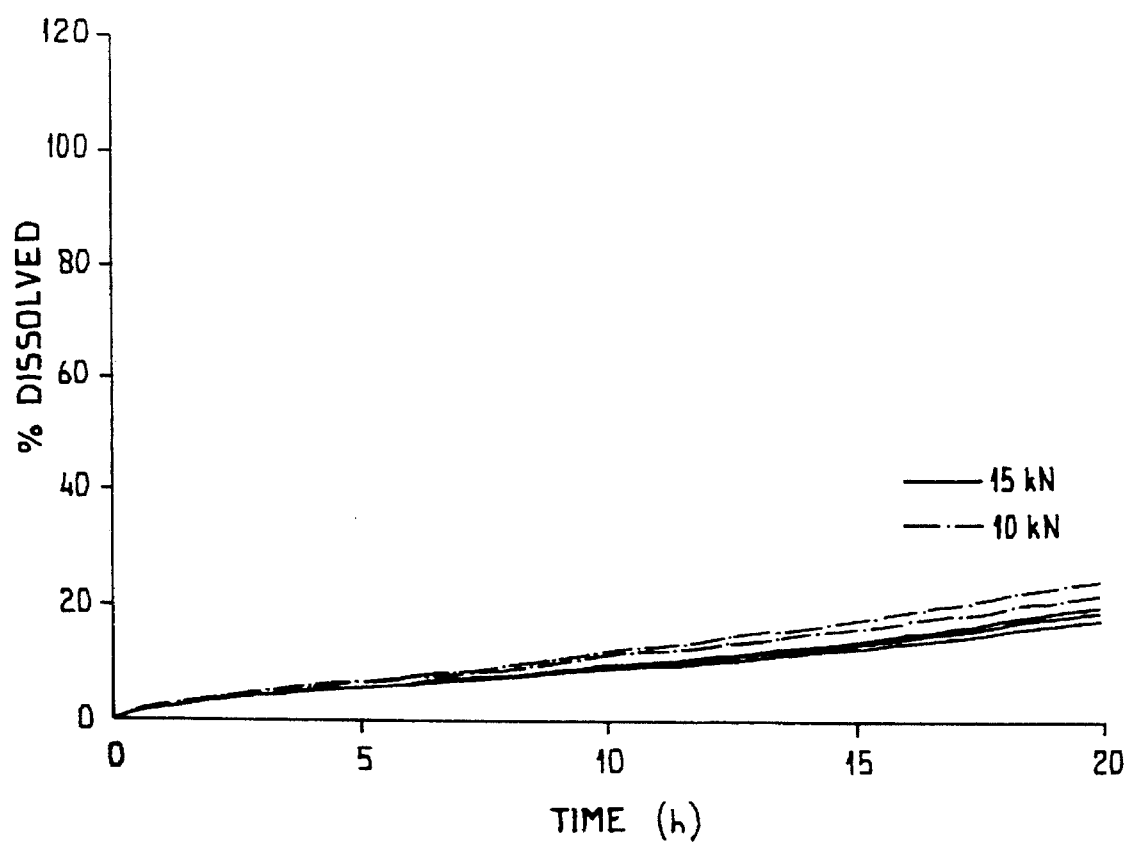
FIG. 11 is a graph of the release of atrazine.

The release of atrazine from amylodextrin matrix tablets containing 30% by weight of active substance was determined. After mixing amylodextrin and atrazine, tablets were struck under a force of, respectively, 10 kN and 15 kN. The tablets weighed 300 Mg, comprising 90 mg of atrazine (=30%), and had a diameter of 9 mm. Release of the active substance from the tablet was determined in an aqueous medium, buffer pH 6.8, over a period of 22 hours and is shown in FIG. 11.

EXAMPLE XI 100 g of amylodextrin were stirred with 2 g of carvone in a round-bottomed flask. Tablets 13 in cross section weighing 300 mg were pressed in a press mould (Specac Ltd, Kent, GB) from the mixture thus obtained. Pressing time 5 min; pressing force varying from 5 to 50 kN.

Figure 12:
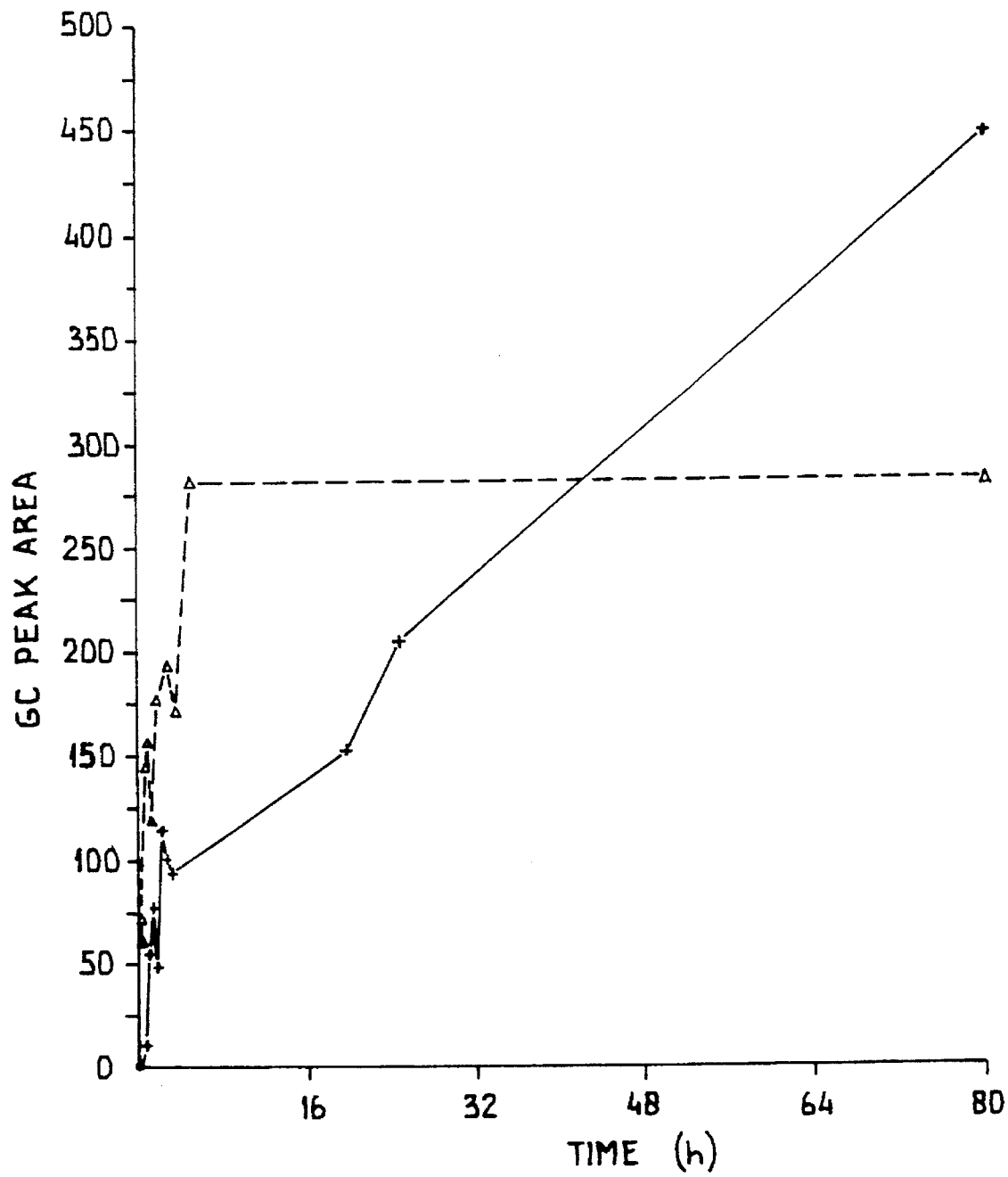
FIG. 12 is a graph of the release profiles of pressed tablets (+) and powder (Δ) for carvone.

The release of carvone into the gas phase was determined in 5-liter flasks sealed by a septum. Gas samples were taken from the flask using a syringe and were analysed using a gas chromatograph (GC column: 10% FFAP on Chrom WAW 80–100 mesh; injector 240° C.; column 160° C.; detector 280° C.; gas flow 45 ml/min; reference: 10 mM carvone solution in ethanol). The release profile of a tablet pressed under a force of 50 kN (+) and, for comparison, of a powder (Δ) is shown in FIG. 12. A relatively rapid release was observed over the first 2 hours, followed by a period of at least 80 hours of slow zero order rate release. Over a period of 80 hours approximately 1.7–2.5 mg of the total amount of the 6 mg of carvone had been released from the tablet, which corresponds to a release rate of approximately $2.1-3.1 * 10^{-5}$ g/h per tablet, or approximately 8–14 µg/cm$^2$.h. The controlled release of carvone is important for the preservation of, for example, potatoes. The release rate can also be controlled by changing the porosity and loading of the tablets.

EXAMPLE XII

Preparation of amylose with a helical structure (metastable form):

a) Starch fractionation:

In 1 liter of water containing 22 ml of 2-methyl-1-butanol, 100 g of starch is dissolved at 160° C. For stabilisation of the starch 0.1 wt. % of sodium sulphite is added. After cooling the solution the crystalline amylose-methylbutanol complex precipitates. The precipitate is collected by centrifugation and washed several times with a solution of 2-methyl-1-butanol in order to remove the amylopectin (being dissolved). The water in the complex is subsequently removed by washing the complex with ethanol en centrifugation (first time) or filtration. In this way the complex is converted to the crystalline amylose-ethanol complex. The so-called metastable form (so-called because the amylose in this form is temporarily soluble in cold water) is obtained by removing the ethanol in vacuo (1 mm Hg) at 50° C. in the presence of phosphorus pentaoxide.

b) Amylose fractionation:

If amylose is chosen as raw material the washing steps needed to remove the amylopectin may be omitted. For the remainder, the procedure is similar as described above.

It may be noted that many other complexing agents may be used instead of 2-methyl-1-butanol. However, the critical concentration of each complexing agent should be taken into account: with starch the critical concentration is used, and with amylose the critical or a higher concentration may be used. The critical concentration of a number of complexing agents is summarised below (form J. Muetgeert, *Advances in Carbohydrate Chemistry*, Vol. 16, Acad. Press (1961), p. 300–305): complexing agent (critical concentration in g per 100 ml of water):

| | |
|---|---|
| 1-butanol (4.2) | isopropyl ketone (0.6) |
| amyl alcohol (1.8) | cyclohexanol (0.5) |
| 1-hexanol (0.3) | phenol (2.5) |
| 2-octanol (0.04) | quinoline (0.6) |
| chloral hydrate (5–8) | butyric acid (11) |

EXAMPLE XIII

Figure 13:
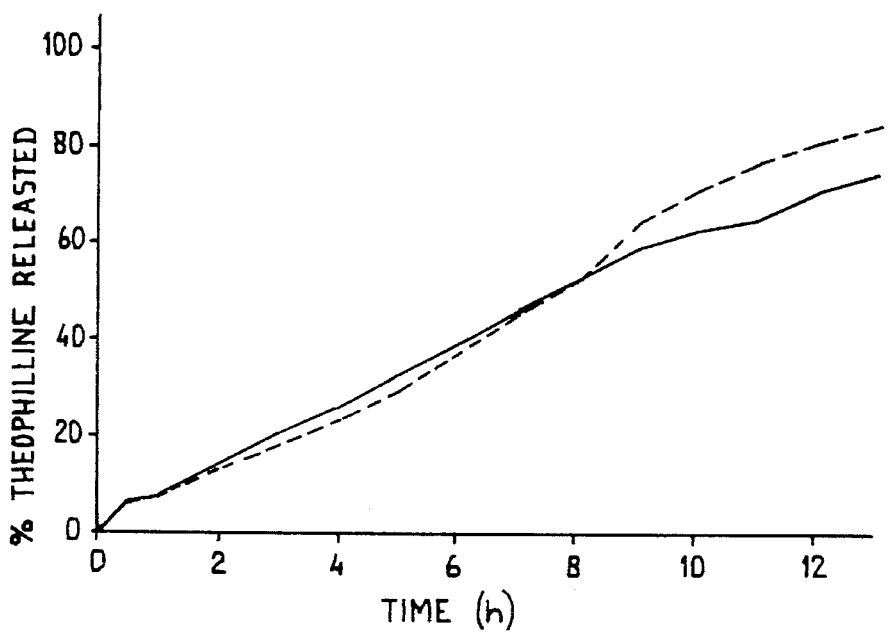
FIG. 13 is a graph of the release of 2% (solid line) and 10% (broken line) theophylline-monohydrate.

Tablets of helical amylose (crystalline amylose, prepared according to example XII), containing 2% or 10% by weight respectively of theophylline-monohydraat were prepared. After mixing granulated crystalline amylose and the appropriate amount theophylline, tablets were struck under a force of 10 kN. The tablets weighed 300 mg, comprising 6 or 30 mg of theophylline and had a diameter of 9 mm. Release of the active substance from the tablet was determined in an aqueous medium, buffer pH 6, over a period of 13 hours and is shown in FIG. 13. This figure shows a zero order release, both for the 2% tablet (solid line) and for the 10% tablet (broken line).

EXAMPLE XIV

Figure 14:
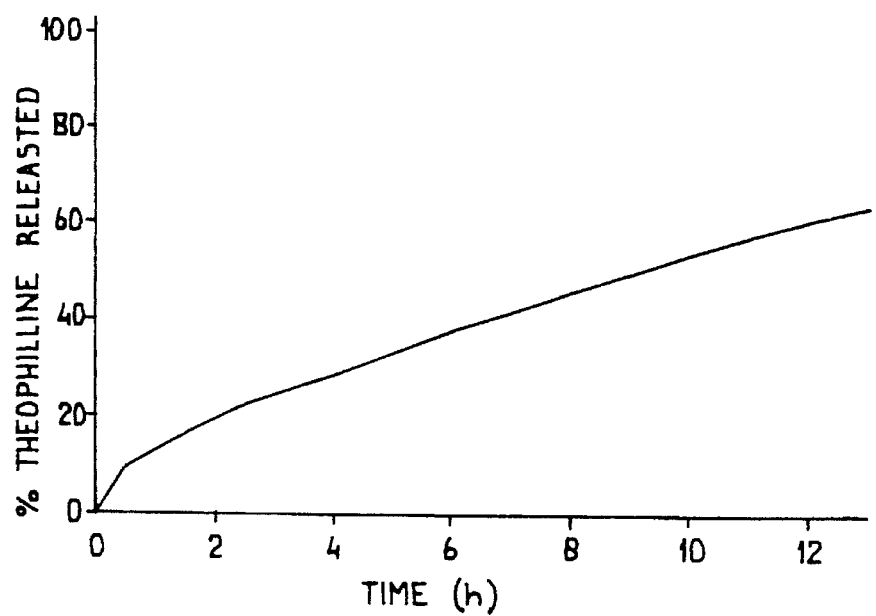
FIG. 14 is a graph of the release of 10% theophylline-monohydrate from tablets.

Tablets of helical amylose (crystalline amylose, prepared according to Example XII), containing or 10% by weight of theophylline-monohydraat were prepared. After mixing dry granulated ("slugged") crystalline amylose and the appropriate amount theophylline, tablets were struck under a force of 10 kN. The tablets weighed 300 mg, comprising 30 mg of theophylline and had a diameter of 9 mm. Release of the active substance from the tablet was determined in an aqueous medium, buffer pH 6, over a period of 13 hours and is shown in FIG. 14. This figure shows a zero order release.

We claim:

1. Composition for controlled release of an active substance at a substantially zero order rate, the active substance being incorporated in a matrix material comprising a polysaccharide, wherein the matrix material comprises at least 50% by weight of a crystalline, straight-chain α-glucan having essentially a helix structure, and the active substance is present in an amount of 0.1–80% by weight of the composition.

2. Composition according to claim 1, wherein the matrix material comprises amylodextrin or a fraction obtained from amylose which has a helix structure.

3. Composition according to claim 1, wherein the matrix material contains 5–25% by weight of water.

4. Composition according to claim 1, which also contains at least one auxiliary which modifies the release pattern.

5. Composition according to claim 1, wherein the active substance is present in an amount of 0.5–50% by weight of the composition.

6. Composition according to claim 1, wherein the active substance has a molecular weight of less than 1,500 daltons.

7. Composition according to claim 1, wherein the active substance is a medicament.

8. Method for the preparation of a composition according to claim 1, wherein a crystalline straight-chain α-glucan having essentially a helix structure is granulated and mixed, before or after granulating, with an active substance and the granulated mixture is brought into the desired form.

9. A method as claimed in claim 8, wherein said desired form is a tablet.

10. Composition according to claim 1, wherein the active substance has a molecular weight of less than 1,000 daltons.

\* \* \* \* \*